US012661086B2

(12) United States Patent
Eda

(10) Patent No.: US 12,661,086 B2
(45) Date of Patent: Jun. 23, 2026

(54) PROBE CABLE HOOK AND CABLE HOLDING STRUCTURE

(71) Applicant: FUJIFILM Healthcare Corporation, Chiba (JP)

(72) Inventor: Masato Eda, Chiba (JP)

(73) Assignee: FUJIFILM Corporation, Tokyo (JP)

( * ) Notice: Subject to any disclaimer, the term of this patent is extended or adjusted under 35 U.S.C. 154(b) by 86 days.

(21) Appl. No.: 18/641,423

(22) Filed: Apr. 21, 2024

(65) Prior Publication Data

US 2024/0374236 A1     Nov. 14, 2024

(30) Foreign Application Priority Data

May 10, 2023     (JP) ................................. 2023-077681

(51) Int. Cl.
A61B 8/00          (2006.01)
(52) U.S. Cl.
CPC .......... A61B 8/4209 (2013.01); A61B 8/4405 (2013.01); A61B 2562/222 (2013.01)
(58) Field of Classification Search
CPC ................ A61B 8/4209; A61B 8/4405; A61B 2562/222; A61B 8/4444; A61B 90/00
See application file for complete search history.

(56) References Cited

U.S. PATENT DOCUMENTS 6,382,571 B1 *   5/2002   Gretz ..................... F16L 3/233
                                                    174/72 A

FOREIGN PATENT DOCUMENTS

WO          2014207593          12/2014

* cited by examiner

*Primary Examiner* — Michael J Carey
*Assistant Examiner* — Zainab Mohammed Aldarraji
(74) *Attorney, Agent, or Firm* — JCIPRNET

(57)          ABSTRACT

Provided is a cable hook capable of more appropriately holding a probe cable. A probe cable hook includes: an attachment portion; a hook portion consisting of a flexible material; and a connecting portion that connects the attachment portion and the hook portion, in which the hook portion has a wrapping portion capable of forming a loop for holding a probe cable, the wrapping portion being formed with an engagement hole, and a head portion that is provided on an opposite side of the connecting portion with respect to the wrapping portion and is engageable with the engagement hole, and the loop is maintained by the head portion being engaged with the engagement hole, and the head portion is detached from the engagement hole by the wrapping portion receiving an outward force in a radial direction of the loop.

8 Claims, 9 Drawing Sheets

LENGTH
DIRECTION

THICKNESS
DIRECTION

WIDTH
DIRECTION

LENGTH
DIRECTION

THICKNESS
DIRECTION

WIDTH
DIRECTION

LENGTH
DIRECTION

THICKNESS
DIRECTION

WIDTH
DIRECTION

ENLARGED PORTION A

LENGTH
DIRECTION

THICKNESS
DIRECTION

WIDTH
DIRECTION

LENGTH
DIRECTION

THICKNESS
DIRECTION

WIDTH
DIRECTION

PROBE CABLE HOOK AND CABLE HOLDING STRUCTURE

CROSS-REFERENCE TO RELATED APPLICATION

The present application claims priority under 35 U.S.C § 119(a) to Japanese Patent Application No. 2023-077681 filed on May 10, 2023 which is hereby expressly incorporated by reference, in its entirety, into the present application.

BACKGROUND OF THE INVENTION

1. Field of the Invention

The present specification discloses a probe cable hook for holding an ultrasound probe and a cable holding structure using the probe cable hook.

2. Description of the Related Art

In the related art, an ultrasound diagnostic apparatus that transmits and receives ultrasonic waves to and from a subject (for example, a living body) and forms an ultrasound image such as a tomographic image based on a reception signal obtained by the transmission and reception of the ultrasonic waves is widely known. An ultrasound probe is connected to the ultrasound diagnostic apparatus via a probe cable. In general, the probe cable has a certain length such that the ultrasound probe can be used even at a place distant from the ultrasound diagnostic apparatus. Therefore, unless special measures are taken, a part of the probe cable often hangs down to a floor surface.

In a case where work related to ultrasound diagnosis is performed while the probe cable hangs down to the floor surface, the probe cable is stepped on by an operator, entangled with another probe cable, or entangled in casters of the ultrasound diagnostic apparatus.

In order to avoid such a problem, an instrument that temporarily holds a probe cable has been proposed in the related art.

For example, WO2014/207593A discloses a cable support having a plastic clip that is mounted on an operation panel, a strap that hangs from a mounting portion, and a cable clip that is connected to a lower end of the strap. In WO2014/207593A, the probe cable is held by the cable clip.

SUMMARY OF THE INVENTION

However, in WO2014/207593A, the cable clip is a substantially U-shaped member that is open upward and has elasticity, and the probe cable is held by the cable clip. In this case, even in a case where the probe cable is strongly pulled, the probe cable cannot be detached from the cable clip, and there is a concern that the probe cable may be deteriorated or damaged.

Therefore, the present specification discloses a cable hook and a cable holding structure capable of more appropriately holding the probe cable.

A probe cable hook disclosed in the present specification comprises: an attachment portion that is attachably and detachably mounted on a part of an ultrasound diagnostic apparatus; a hook portion consisting of a flexible material; and a connecting portion that connects the attachment portion and the hook portion, in which the hook portion has a wrapping portion capable of forming a loop for holding a probe cable of an ultrasound probe, the wrapping portion being formed with an engagement hole, and a head portion that is provided on an opposite side of the connecting portion with respect to the wrapping portion and is engageable with the engagement hole, and the loop is maintained by the head portion being engaged with the engagement hole, and the head portion is detached from the engagement hole by the wrapping portion receiving an outward force in a radial direction of the loop.

According to the probe cable, since the loop for holding the probe cable is easily released by receiving a strong force, the wrapping portion is prevented from biting into the probe cable. As a result, it is possible to more appropriately hold the probe cable.

In this case, the head portion may be wider than the wrapping portion, a constricted portion having a smaller width than the wrapping portion may be formed at a boundary between the head portion and the wrapping portion, and a width of the constricted portion may be the same as or smaller than a width of the engagement hole.

With the above-described dimension, the head portion is easily caught in the engagement hole. As a result, unintended detachment from the engagement hole of the head portion is prevented.

In addition, the head portion may have a substantially columnar shape having an axis extending in a width direction, and a diameter of the head portion may decrease toward a width direction end part.

With the above-described shape, the head portion is easily detached from the engagement hole before an excessive force is applied to the probe cable.

In addition, the engagement hole may have a long hole shape in which a length direction dimension is larger than a width direction dimension, and a side portion, which is a portion between a width direction end part of the hook portion and a width direction end part of the engagement hole, may have a length direction dimension larger than a width direction dimension.

By making the engagement hole long in the length direction, a difference in thickness of the probe cable can be absorbed in the engagement hole. In addition, by making the engagement hole long in the length direction and making the side portion also elongated in the length direction, the side portion is easily stretched, and the engagement hole is easily deformed. As a result, the head portion is easily detached from the engagement hole before an excessive force is applied to the probe cable.

In addition, the connecting portion may consist of a flexible material and may be narrower than the hook portion.

In a case where the connecting portion is supplemented, the connecting portion is easily stretched. As a result, a movable range of the hook portion is widened, and the hook portion easily follows the movement of the ultrasound probe.

In addition, the attachment portion, the hook portion, and the connecting portion may be integrally formed by a flexible material.

By performing the integral forming, it is possible to simplify a manufacturing process of the probe cable hook.

In addition, the probe cable hook may have a shape that is line-symmetric with respect to a center in a width direction as a symmetry axis and is line-symmetric with respect to a center in a thickness direction as a symmetry axis.

The probe holder that holds the ultrasound probe is disposed on left and right sides of the diagnostic apparatus in many cases. With the above configuration, one probe cable hook can be applied to both the left and right probe holders without considering the direction.

In addition, the attachment portion may be engageable with a bottom surface of a probe holder that holds the ultrasound probe, and the probe cable hook may be held by being suspended from the probe holder.

By adopting a configuration in which the probe cable hook is mounted on the probe holder, one probe cable hook can be attached to one ultrasound probe. Accordingly, it is possible to prevent a plurality of probe cables from being concentrated and entangled at one place. In addition, by engaging the attachment portion with the bottom surface of the probe holder, the probe cable hook does not interfere with work of inserting and pulling out the ultrasound probe into and from the probe holder.

A cable holding structure disclosed in the present specification comprises: the above-described probe cable hook; and the probe holder that holds the ultrasound probe in a standing posture such that a cable draw-out portion of the ultrasound probe faces downward, in which the attachment portion has a larger size than the connecting portion in at least one of a width direction dimension or a thickness direction dimension, the probe holder has an outer cup and an inner cup that is disposed inside the outer cap, and a cable hole allowing passage of the probe cable, an accommodation recessed portion that accommodates the attachment portion, and a connection notch that extends over the cable hole and a bottom surface of the accommodation recessed portion and allows passage of the connecting portion are formed on a bottom surface of the outer cup.

With the above configuration, it is possible to attach the probe cable hook to the probe holder by a simple procedure. In addition, since the accommodation recessed portion is formed in the outer cup, the attachment portion of the probe cable hook does not interfere with the inner cup, and the inner cup does not rattle.

According to the probe cable hook and the cable holding structure disclosed in the present specification, it is possible to more appropriately hold the probe cable.

DESCRIPTION OF THE PREFERRED EMBODIMENTS

Figure 1:
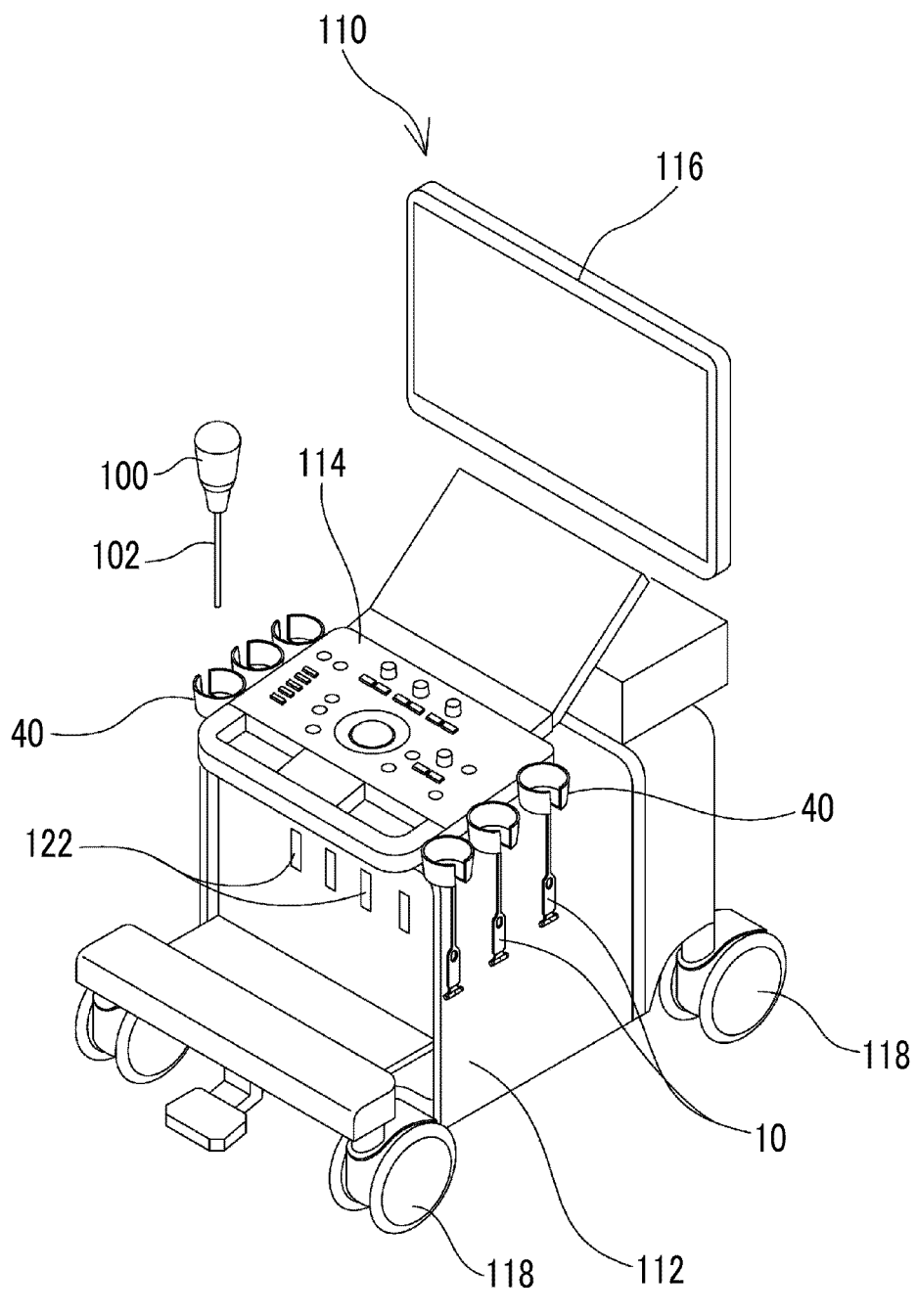
FIG. 1 is a perspective view of an ultrasound diagnostic apparatus.

Hereinafter, configurations of a probe cable hook 10 and a cable holding structure will be described with reference to the drawings. FIG. 1 is a schematic perspective view of an ultrasound diagnostic apparatus 110 to which the probe cable hook 10 is attached.

The ultrasound diagnostic apparatus 110 transmits and receives ultrasonic waves to and from a subject (for example, a living body) and forms an ultrasound image such as a tomographic image based on a reception signal obtained by the transmission and reception of the ultrasonic waves. The ultrasound diagnostic apparatus 110 includes a body part 112, an operation panel 114, and a display 116. The body part 112 is a main part of the ultrasound diagnostic apparatus 110, and is a base that supports the operation panel 114 and the display 116. The body part 112 is supported by casters 118, whereby the ultrasound diagnostic apparatus 110 can be easily moved on a floor surface.

An ultrasound probe 100 is connected to the body part 112 via a probe cable 102. A plurality of connection terminals 122 to which a connection terminal (not shown) of the probe cable 102 is connected are provided on a front surface of the body part 112.

The operation panel 114 receives an operation input from a user. The operation panel 114 includes various operation buttons, a trackball, and the like. The display 116 displays the ultrasound image and various kinds of information. Both the operation panel 114 and the display 116 are attached to a multi-joint arm (not shown). Then, the user can freely change a position and a posture of the operation panel 114 and the display 116 by changing a posture of the multi-joint arm.

The ultrasound diagnostic apparatus 110 is further provided with a plurality of probe holders 40. The probe holder 40 holds the ultrasound probe 100 in a standing posture such that a cable draw-out portion of the ultrasound probe 100 faces downward. Such a probe holder 40 is attached to a periphery of the ultrasound diagnostic apparatus 110. In a case of the example in FIG. 1, a plurality of (three in the illustrated example) the probe holders 40 are attached to each of left and right sides of the operation panel 114.

As will be described in detail below, the probe holder 40 has a substantially cup shape in which a hole is formed in a bottom surface. The ultrasound probe 100 is inserted into the probe holder 40 in a standing posture. The probe cable 102 is drawn out downward from the hole formed in the bottom surface of the probe holder 40. In a case where the ultrasound diagnosis is performed, a diagnostician selects the ultrasound probe 100 suitable for the diagnosis from among the ultrasound probes 100 held by the plurality of probe holders 40, and extracts the selected ultrasound probe 100 from the probe holder 40. Then, the diagnostician acquires an ultrasound image by bringing the extracted ultrasound probe 100 into contact with a diagnosis site.

Here, the probe cable 102 has a sufficient length so that the ultrasound probe 100 can be carried to a place distant from the ultrasound diagnostic apparatus 110. Therefore, unless special measures are taken, a part of the probe cable 102 often hangs down to a floor surface. In a case where work related to ultrasound diagnosis is performed while the probe cable 102 hangs down to the floor surface as described above, the probe cable 102 is stepped on by a person, entangled with another probe cable 102, or entangled in the casters 118 of the ultrasound diagnostic apparatus 110. As a result, in a case where the probe cable 102 is left in a state of hanging down to the floor surface, the probe cable 102 may be deteriorated or damaged.

The probe cable hook 10 is attached to the ultrasound diagnostic apparatus 110 in order to prevent the probe cable 102 from hanging down. The probe cable hook 10 is a member that prevents the probe cable 102 from hanging down by holding a part of the probe cable 102 in a state of being attached to the ultrasound diagnostic apparatus 110. The attachment position of the probe cable hook 10 is not particularly limited as long as a part of the probe cable 102 can be held. In a case of the example in FIG. 1, the probe cable hook 10 is attached to the bottom surface of the probe holder 40. Hereinafter, the configuration of the probe cable hook 10 will be described in detail.

Figure 2:
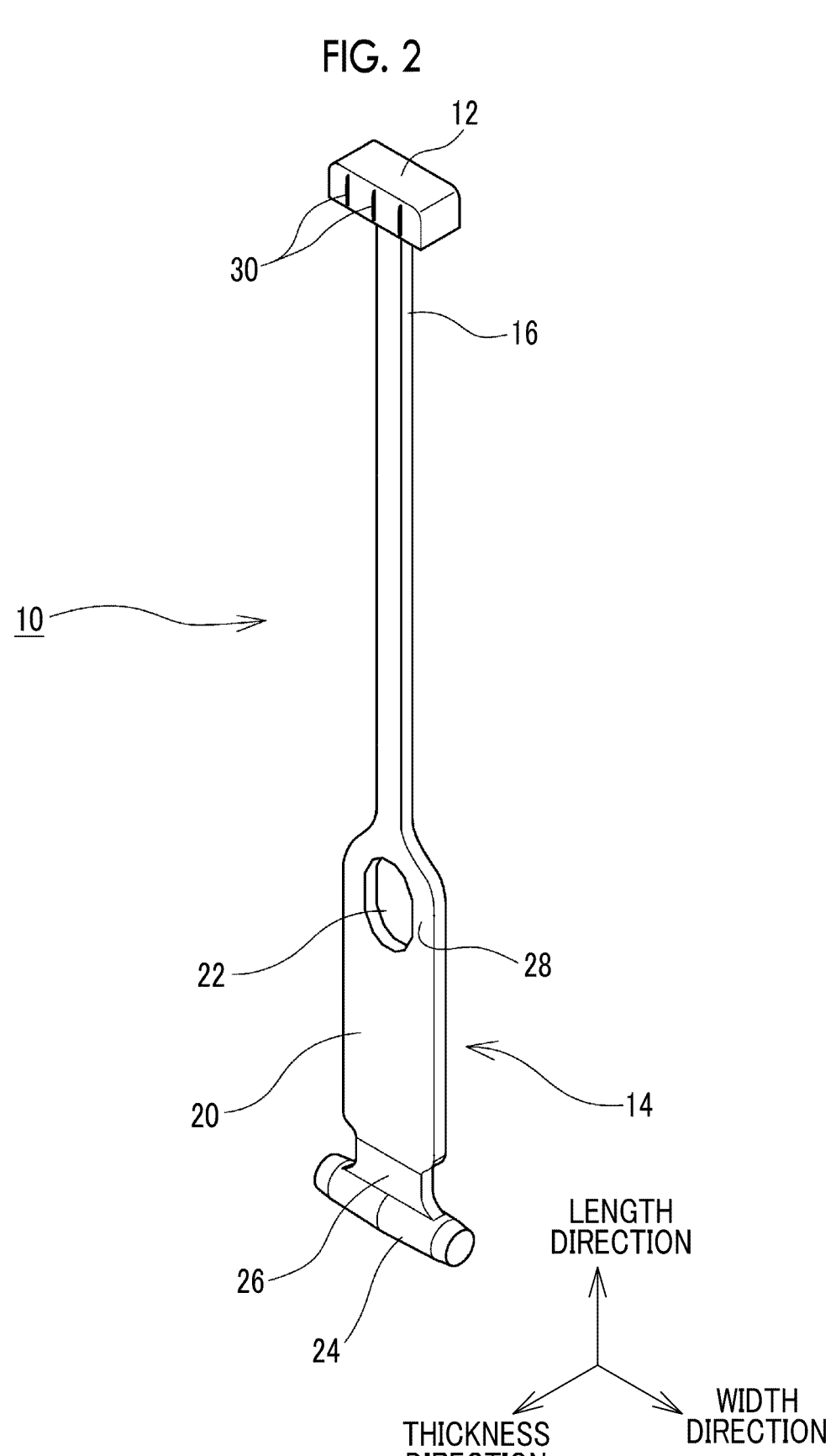
FIG. 2 is a perspective view of a probe cable hook.
Figure 3:
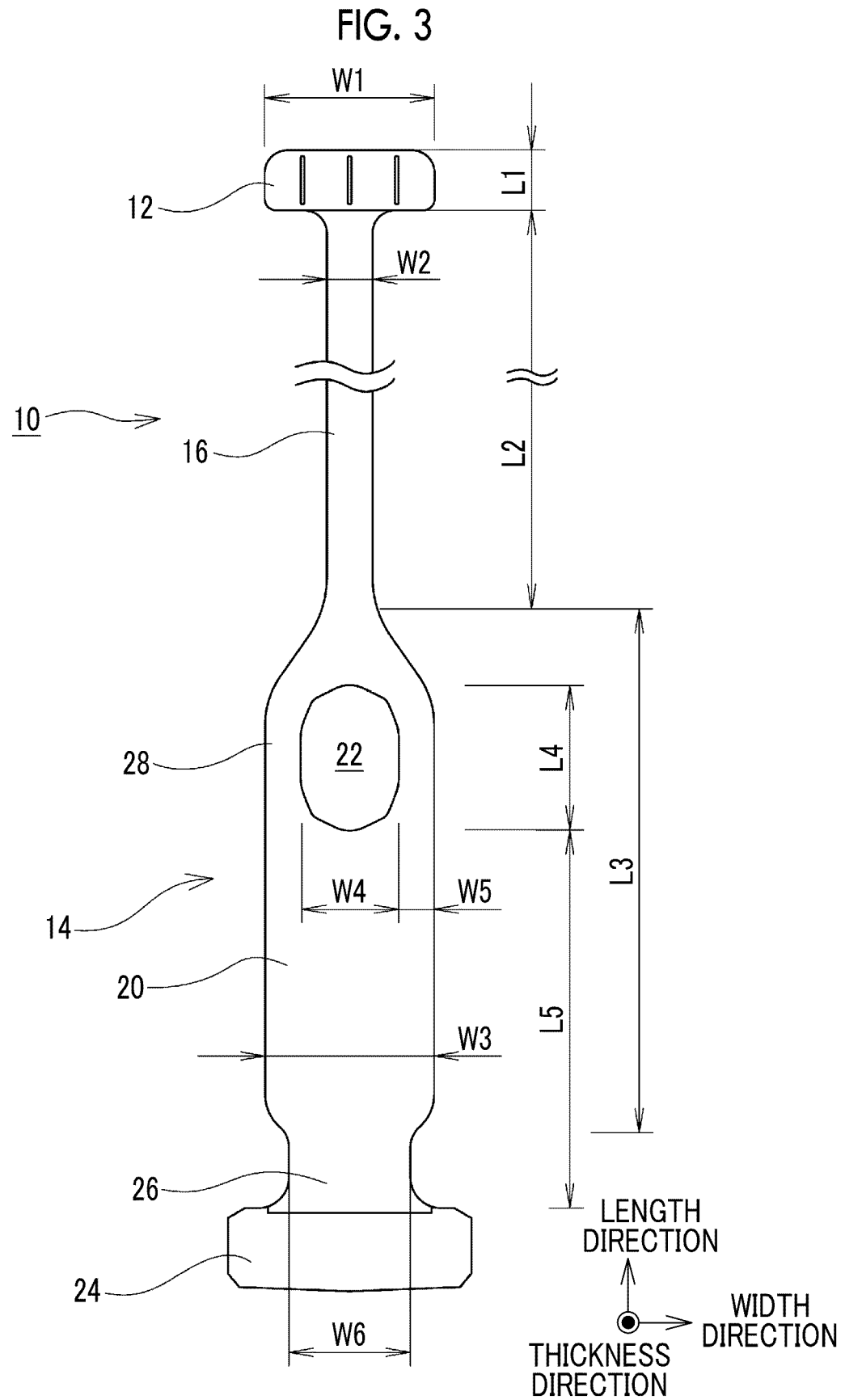
FIG. 3 is a front view of the probe cable hook.

FIG. 2 is a perspective view of the probe cable hook 10, and FIG. 3 is a front view of the probe cable hook 10. In the following description, a direction from an attachment portion 12 toward the hook portion 14 is referred to as a "length direction", and a direction orthogonal to both a plate thickness direction and a length direction of the probe cable hook 10 is referred to as a "width direction".

The probe cable hook 10 is roughly divided into the attachment portion 12, the hook portion 14, and a connecting portion 16. The attachment portion 12, the hook portion 14, and the connecting portion 16 are integrally formed of a flexible material. As the flexible material constituting the probe cable hook 10, for example, silicone rubber or natural rubber can be employed. In this example, the probe cable hook 10 is made of highly extensible silicone rubber having excellent extensibility.

The attachment portion 12 is a portion attached to the bottom surface of the probe holder 40. The attachment portion 12 has a block shape wider and thicker than the connecting portion 16. A plurality of (three in the illustrated example) friction protrusions 30 for increasing a friction coefficient are formed on both end surfaces of the attachment portion 12 in the plate thickness direction.

The connecting portion 16 is a strap-shaped portion that extends downward from a bottom surface of the attachment portion 12 and connects the attachment portion 12 and the hook portion 14. The connecting portion 16 has a length direction dimension L2 that is sufficiently longer than a width direction dimension W2. For example, the length direction dimension L2 of the connecting portion 16 is equal to or more than 10 times the width direction dimension W2. By making the connecting portion 16 have an elongated strap shape, the connecting portion 16 is easily stretched and easily curved in various directions. As a result, a degree of freedom of movement of the hook portion 14 with respect to the attachment portion 12 is improved.

The hook portion 14 is a portion that holds the probe cable 102. The hook portion 14 is further roughly divided into a wrapping portion 20 and a head portion 24. The wrapping portion 20 has a band shape wider than the connecting portion 16 and is a portion that is wound around the probe cable 102. An engagement hole 22 is formed in an upper portion of the wrapping portion 20, that is, in a portion close to a joint with the connecting portion 16. The engagement hole 22 is a hole into which the head portion 24 is inserted and engaged. A shape of the engagement hole 22 is not particularly limited as long as the head portion 24 can be inserted into and engaged with the engagement hole 22. In this example, the engagement hole 22 has a substantially elliptical shape or a substantially rectangular shape in which a length direction dimension L4 is larger than a width direction dimension W4. In this way, by making the engagement hole 22 a long hole that is elongated in the length direction, the probe cables 102 of various diameters can be appropriately held. This will be described below.

A side portion 28 is formed between a width direction end part of the engagement hole 22 and a width direction end part of the wrapping portion 20. As shown in FIG. 3, the side portion 28 has a length direction dimension L4 that is sufficiently larger than a width direction dimension W5. By making the side portion 28 elongated in the length direction, the side portion 28 is easily stretched compared to other portions, and the engagement hole 22 is easily deformed. As a result, the insertion of the head portion 24 into the engagement hole 22 and the detachment of the head portion 24 from the engagement hole 22 are facilitated. This will be described below.

A distance L5 from a lower end of the engagement hole 22 to a lower end of the wrapping portion 20 is determined in consideration of the diameter of the probe cable 102 to be handled. For example, in a case where the maximum diameter of the probe cable 102 to be handled is denoted by Dmax, the distance L5 is larger than the circumference of the probe cable 102, that is, (π×Dmax). With such a dimension, the probe cable 102 having the maximum diameter can be appropriately held by the probe cable hook 10.

The head portion 24 is formed at a lower end of a constricted portion 26 and is a portion that is inserted into and engaged with the engagement hole 22. A shape of the head portion 24 is not particularly limited as long as the head portion 24 is wider than the engagement hole 22. In this example, the head portion 24 is wider than the wrapping portion 20. More specifically, the head portion 24 has a substantially cylindrical shape having an axis extending in the width direction. A diameter of the head portion 24 gradually decreases toward a width direction end part.

The constricted portion 26 is provided between the wrapping portion 20 and the head portion 24. A width direction dimension W6 of the constricted portion 26 is substantially the same as the width direction dimension W4 of the engagement hole 22 or is smaller than the width direction dimension W4 of the engagement hole 22.

Figure 4:
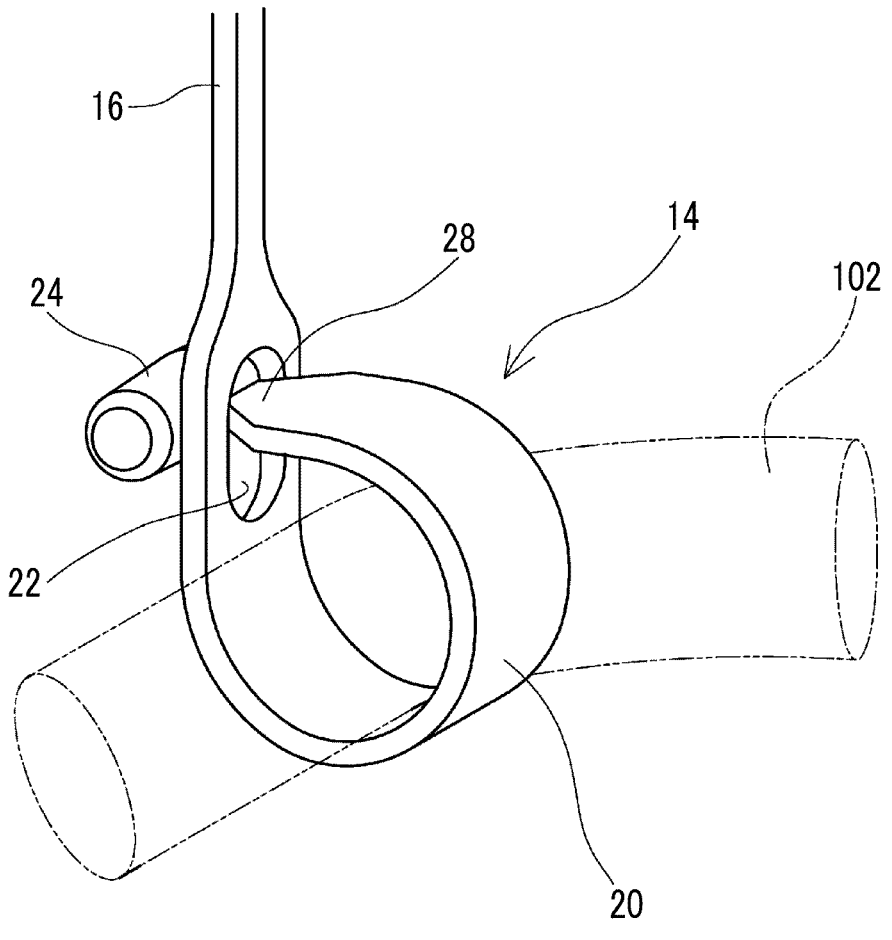
FIG. 4 is a perspective view showing a state in which a probe cable is held by a hook portion.

The probe cable hook 10 having the above configuration is attached to the bottom surface of the probe holder 40, and is held by being suspended from the probe holder 40. FIG. 4 is a schematic view showing a state in which the probe cable 102 is held by the hook portion 14. As shown in FIG. 4, in a case where the probe cable 102 is held by the hook portion 14, the wrapping portion 20 is wound around the probe cable 102 such that a loop is formed by the wrapping portion 20. In this state, the head portion 24 is inserted into the engagement hole 22. Here, the head portion 24 is wider than the engagement hole 22. Note that since a surrounding material of the engagement hole 22 is relatively easily stretched, the engagement hole 22 is easily deformed so that the head portion 24 can pass therethrough. In a case where the head portion 24 completely passes through the engagement hole 22, as shown in FIG. 4, the constricted portion 26 is positioned inside the engagement hole 22. The constricted portion 26 has substantially the same width as the engagement hole 22 or a smaller width than the engagement hole 22. Therefore, in a case where the head portion 24 passes through the engagement hole 22, the engagement hole 22 returns to the original shape by an elastic restoration force. In this state, the head portion 24 is engaged with the engagement hole 22, and thus the loop by the wrapping portion 20 is maintained. The probe cable 102 is held in the loop.

Figure 5:
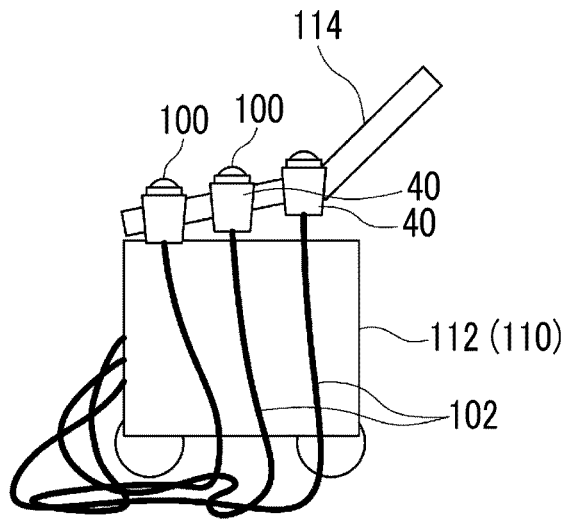
FIG. 5 is a diagram showing a difference in route of the probe cable depending on the presence or absence of the probe cable hook.
Figure 5:
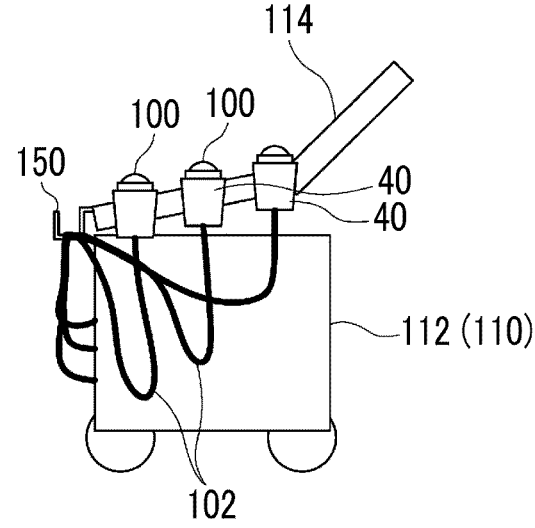

In this way, by holding an intermediate portion of the probe cable 102 by the loop, that is, the probe cable hook 10, it is possible to prevent the probe cable 102 from hanging down to the floor surface. FIG. 5 is a diagram showing a difference in state of the probe cable 102 depending on the presence or absence of the probe cable hook 10. As shown in a middle part of FIG. 5, in a case where the probe cable hook 10 is not provided, the probe cable 102 often hangs down to the floor surface. As described above, in a case where the probe cable 102 hangs down to the floor surface, the probe cable 102 is stepped on by a person, the probe cables 102 are entangled with each other, the probe cable 102 is entangled in the casters 118, and the like.

On the other hand, as shown in an upper part of FIG. 5, in a case where the intermediate portion of the probe cable 102 is held by the probe cable hook 10, the probe cable 102 takes a large detour to pass through the loop portion of the wrapping portion 20 in a process from the ultrasound probe 100 to the connection terminal 122. Accordingly, the extra length portion of the probe cable 102 is effectively prevented from hanging down to the floor surface.

As described repeatedly, the probe cable 102 is attached to the bottom surface of the probe holder 40. In other words, in this example, one probe cable 102 is provided for one ultrasound probe 100. With such a configuration, even in a case where the diagnostician sequentially replaces the ultrasound probe 100 to be used with one another, it is possible to effectively prevent the probe cables 102 from being entangled with each other. That is, in the related art as well, in order to prevent the probe cable 102 from hanging down, a U-shaped hook 150 that holds the extra length portion of the probe cable 102 has been provided.

A lower part of FIG. 5 shows a state in which the intermediate portion of the probe cable 102 is held by the U-shaped hook 150. The U-shaped hook 150 is a substantially U-shaped member that is open upward. Such a U-shaped hook 150 is attached to the periphery of the ultrasound diagnostic apparatus 110, for example, to a peripheral edge of the operation panel 114. The user collectively places the plurality of probe cables 102 on a U-shaped portion of the U-shaped hook 150. With such a U-shaped hook 150 as well, it is possible to prevent the probe cable 102 from hanging down to some extent. However, in the related art, the plurality of probe cables 102 are placed on one U-shaped hook 150. Therefore, each time the user replaces the ultrasound probe 100 to be used, in other words, each time the probe cable 102 pulled by a hand of the user is changed, an up-down relationship of the overlapping probe cables 102 in the U-shaped hook 150 is changed. As a result, in a case of the technique of the related art in which the plurality of probe cables 102 share one U-shaped hook 150, the plurality of probe cables 102 may be complicatedly entangled with each other.

On the other hand, in this example, as described above, one probe cable hook 10 is provided for one ultrasound probe 100. Therefore, even in a case where the user replaces the ultrasound probe 100 to be used, the probe cables 102 is effectively prevented from being entangled with each other.

Meanwhile, during the use of the ultrasound probe 100, the user moves the ultrasound probe 100 to various places. Accordingly, the probe cable 102 may be pulled considerably. In a case of this example, since the connecting portion 16 is elongated, the connecting portion 16 can be easily bent in various directions. Further, in this example, the entire probe cable hook 10 including the connecting portion 16 is made of a highly extensible silicone rubber, and the connecting portion 16 has an elongated shape having an aspect ratio of 10 or more. As a result, the connecting portion 16 can be stretched by 2 to 6 times (for example, 5 times or more) compared to an unloaded state. Accordingly, a movable range of the hook portion 14 is widened, and the hook portion 14 can appropriately follow the movement of the probe cable 102. As a result, with the probe cable hook 10 of this example, the probe cable 102 can be appropriately held without interfering with the operation of the ultrasound probe 100 by the user.

Note that, of course, there is a limitation on the movable range of the hook portion 14. The probe cable 102 may be strongly pulled beyond the movable range. In this case, in a case where the hook portion 14 firmly holds the probe cable 102, the wrapping portion 20 bites into the probe cable 102, and the probe cable 102 may be deteriorated or damaged.

On the other hand, in a case of this example, the wrapping portion 20 is made of a flexible material, and the engagement hole 22 can be easily deformed. As a result, in a case where the probe cable 102 is pulled with a certain degree of strong force, a radially outward force is applied to the loop formed by the wrapping portion 20. In a case where such a radially outward force is applied, the engagement between the engagement hole 22 and the head portion 24 is released, and the holding of the probe cable 102 is released. In particular, as described above, in this example, the side portions 28 positioned on both sides of the engagement hole 22 have an elongated shape in the length direction. By adopting such a shape, the side portion 28 is easily stretched, and the engagement hole 22 is easily deformed. In addition, in this example, the head portion 24 has a shape that decreases in diameter toward both ends in the width direction. In a case of such a shape, the side portion 28 that is strongly pressed against a peripheral surface of the head portion 24 is guided to a tapered surface of the head portion 24 and is easily moved to the outside in the width direction. Then, the side portion 28 is moved to the outside in the width direction, whereby the engagement hole 22 is easily widened. As a result, the engagement between the engagement hole 22 and the head portion 24 is more easily released. Accordingly, it is possible to more effectively prevent the deterioration and damage of the probe cable 102.

Figure 6:
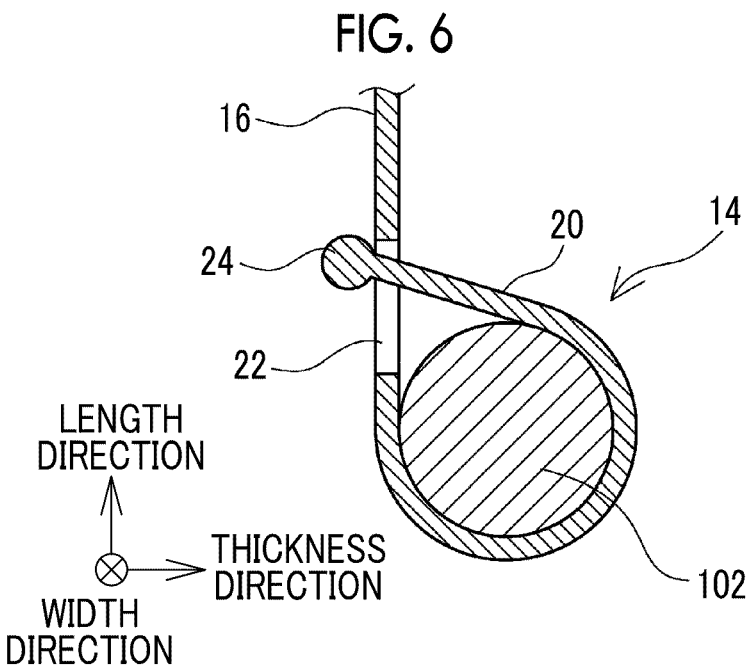
FIG. 6 is a diagram showing a difference in loop due to a difference in diameter of the probe cable.
Figure 6:
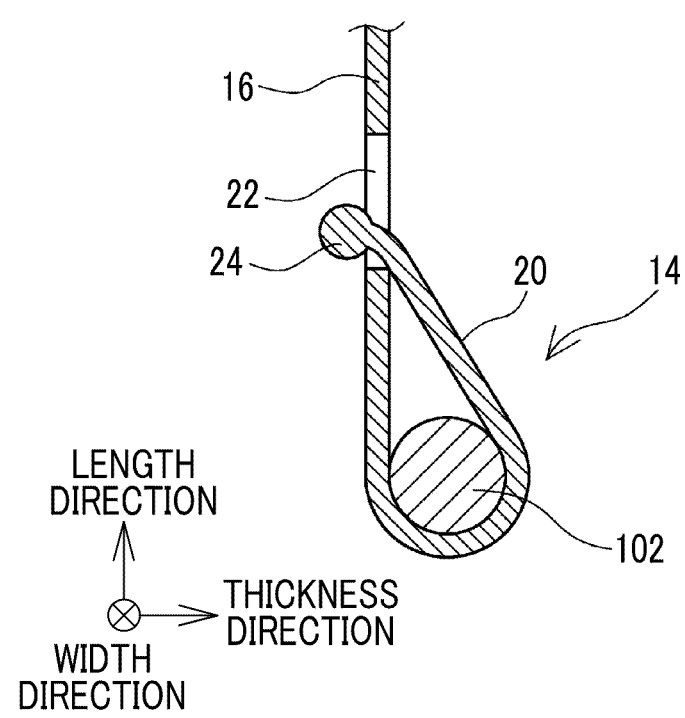

In addition, as described above, the engagement hole 22 is a long hole that is elongated in the length direction. With such a shape, the probe cables 102 of various diameters can be appropriately held. This will be described with reference to FIG. 6. FIG. 6 is a schematic cross-sectional view of a periphery of the hook portion 14. As shown in an upper part of FIG. 6, in a case where the head portion 24 holds the probe cable 102 having a large diameter, the wrapping portion 20 forms a loop having a large diameter, and the head portion 24 is positioned near an upper end of the engagement hole 22. On the other hand, as shown in a lower part of FIG. 6, in a case where the head portion 24 holds the probe cable 102 having a small diameter, the wrapping portion 20 forms a loop having a small diameter. In this case, the loop is pulled downward by the weight of the probe cable 102. Therefore, in this case, the loop has a substantially droplet shape, and the head portion 24 slides down near a lower end of the engagement hole 22.

That is, with a configuration in which the wrapping portion 20 is wound around the probe cable 102 and the head portion 24 is inserted into the engaging part that is a long hole, the shape of the loop and the engagement position of the head portion 24 can be changed according to the diameter of the probe cable 102. As a result, one probe cable hook 10 can handle the probe cables 102 of various diameters. In other words, with the above-described configuration, it is possible to improve general-purpose properties of the probe cable hook 10.

Figure 7:
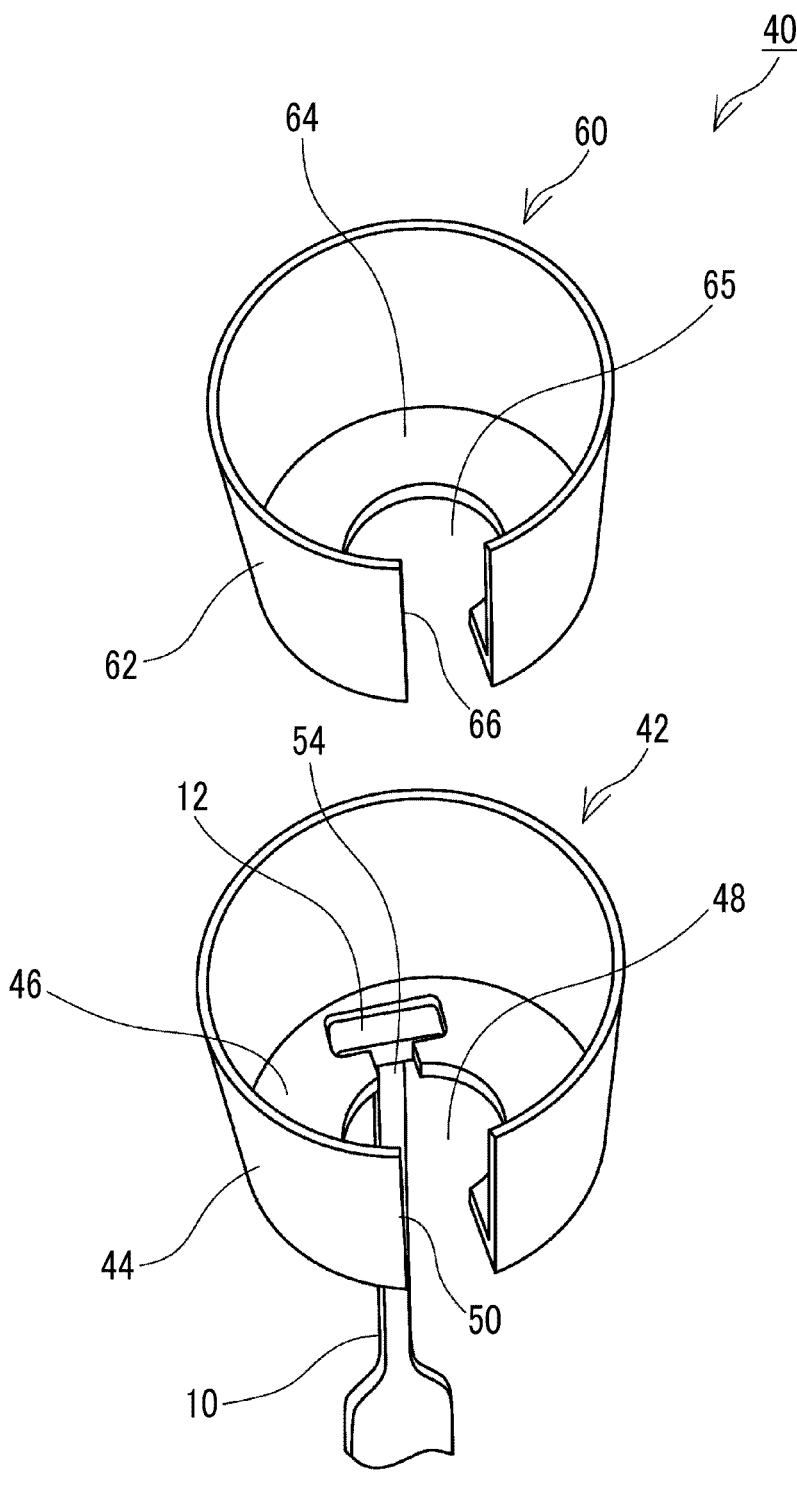
FIG. 7 is a schematic exploded perspective view of a probe holder.
Figure 8:
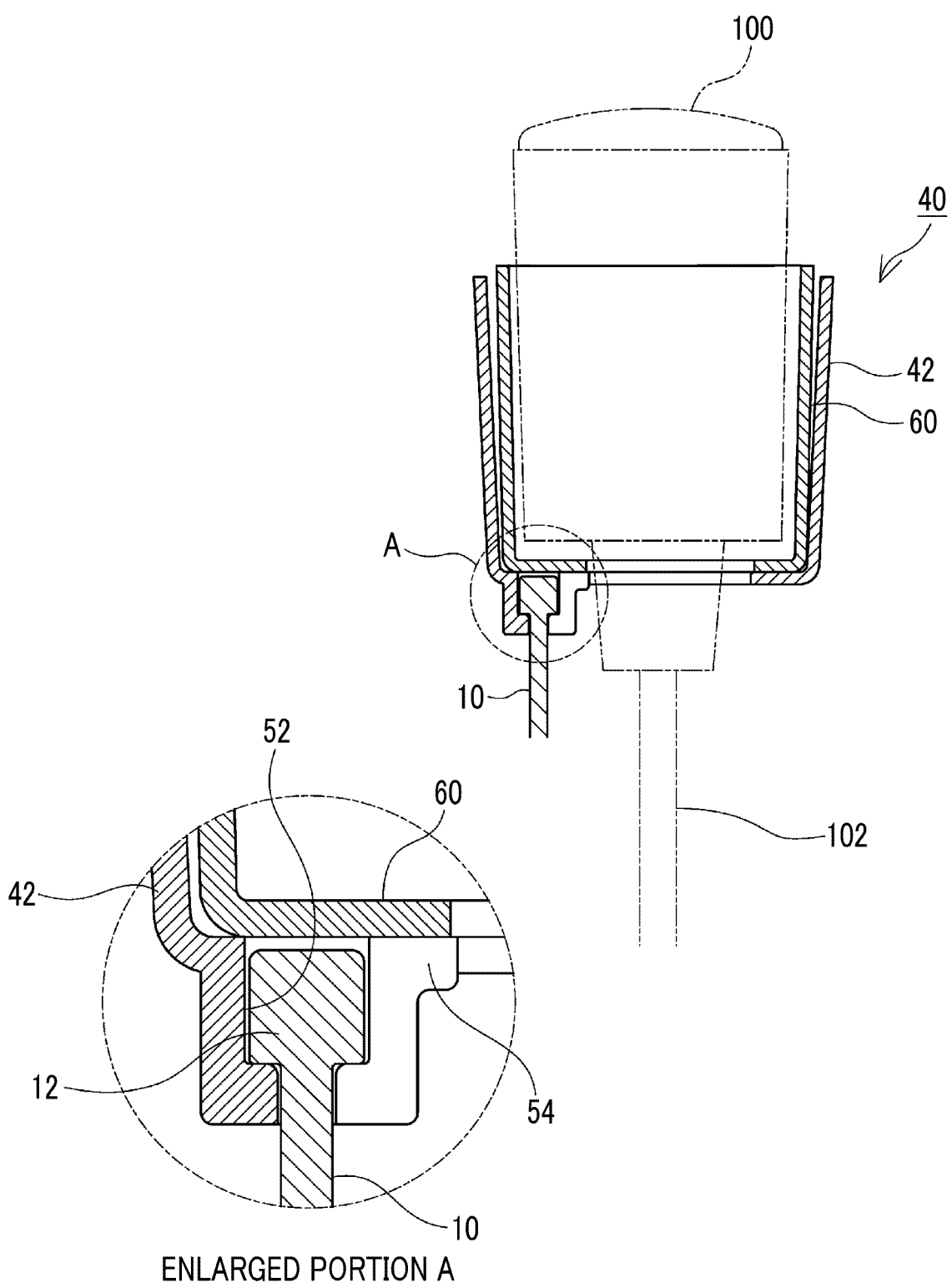
FIG. 8 is a schematic cross-sectional view of the probe holder.

Next, the attachment of the probe cable hook 10 to the probe holder 40 will be described with reference to FIGS. 7 and 8. FIG. 7 is a schematic exploded perspective view of the probe holder 40. In addition, FIG. 8 is a schematic cross-sectional view of a periphery of the accommodation recessed portion 52.

As described above, the probe holder 40 holds the ultrasound probe 100 in a standing posture. The probe holder 40 is roughly divided into an outer cup 42 and an inner cup 60. In FIGS. 7 and 8, the outer cup 42 and the inner cup 60 are shown in a simplified manner, but in practice, the outer cup 42 and the inner cup 60 have a complicated shape having a larger number of uneven parts and protrusions.

The outer cup 42 has a substantially cup shape having a substantially circular plate-shaped bottom wall 46 and a peripheral wall 44 that stands from a peripheral edge of the bottom wall 46. A cable hole 48 that allows passage of the probe cable 102 is formed at the center of the bottom wall 46. Further, an entrance/exit notch 50, which is a notch connected to the cable hole 48, is formed in the peripheral wall 44 and the bottom wall 46. The outer cup 42 is attached to right and left end parts of the operation panel 114.

The inner cup 60 also has a substantially cup shape having a substantially circular plate-shaped bottom wall 64 and a peripheral wall 62 that stands from a peripheral edge of the bottom wall 64, as with the outer cup 42. In addition, in the inner cup 60, a cable hole 65 that allows passage of the probe cable 102 and an entrance/exit notch 66 connected to the cable hole 65 are formed.

In a case where such a probe holder 40 holds the ultrasound probe 100, the inner cup 60 is superposed on the outer cup 42, and phases of the entrance/exit notches 50 and 66 of the both cups 42 and 60 are made to match. Then, the user inserts the probe cable 102 through the entrance/exit notches 50 and 66 and passes the probe cable 102 through the cable holes 48 and 65 in a state where the user holds the ultrasound probe 100 in the hand in a standing posture. Thereafter, the user inserts the ultrasound probe 100 into the inner cup 60 from the upper side. Accordingly, the ultrasound probe 100 is held by the probe holder 40, and the probe cable 102 extends downward from the cable holes 48 and 65.

The attachment portion 12 of the probe cable hook 10 is engaged with a bottom surface of the outer cup 42. Specifically, the bottom wall 46 of the outer cup 42 is further formed with the accommodation recessed portion 52 and a connection notch 54. The accommodation recessed portion 52 is a recessed portion that is depressed downward from the bottom wall 46 and is a recessed portion that completely accommodates the attachment portion 12. The connection notch 54 is a notch that connects the accommodation recessed portion 52 and the cable hole 48.

The attachment portion 12 of the probe cable hook 10 is accommodated in the accommodation recessed portion 52 through the connection notch 54 from the cable hole 48. In this case, the attachment portion 12 is caught on a bottom surface of the accommodation recessed portion 52. As a result, the probe cable hook 10 is held by being suspended from the bottom surface of the probe holder 40. Here, in a case where the attachment portion 12 is accommodated in the accommodation recessed portion 52, the friction protrusion 30 comes into contact with an inner surface of the accommodation recessed portion 52 to generate friction. Accordingly, rattling of the attachment portion 12 in the accommodation recessed portion 52 is suppressed.

In a state where the attachment portion 12 is accommodated in the accommodation recessed portion 52, the inner cup 60 is superposed on the outer cup 42. In other words, the attachment portion 12 is vertically interposed between the outer cup 42 and the inner cup 60. Accordingly, the movement of the attachment portion 12 in the up-down direction is restricted, and unintended detachment of the attachment portion 12 from the accommodation recessed portion 52 and thus unintended falling-off of the probe cable hook 10 from the probe holder 40 can be effectively prevented.

As is clear from the above description, with the configuration of the attachment portion 12 of this example, the probe cable hook 10 can be attached to and detached from the probe holder 40 by an easy procedure without breaking the probe holder 40. In addition, with the above configuration, it is not necessary to change the configuration of the inner cup 60 from the configuration in the related art, and the existing inner cup 60 can be used as it is.

In addition, in a case of the above-described configuration, the probe cable hook 10 hangs down below the bottom surface of the probe holder 40. With such disposition, in a case where the user insets and pulls out the ultrasound probe 100 into and from the probe holder 40, the probe cable hook 10 does not interfere with the work.

The attachment form of the probe cable hook 10 is an example, and may be changed as appropriate. For example, the attachment portion 12 may have a clip shape that is engaged with an upper edge of the peripheral wall 44 or 62 of the outer cup 42 or the inner cup 60. In addition, the attachment portion 12 may be attached to the bottom wall 46 of the outer cup 42 by using a magnetic force. For example, a magnet may be provided in one of the bottom wall 46 and the attachment portion 12, and a magnetic body may be provided in the other. Further, the attachment portion 12 is not limited to the probe holder 40 and may be attached to another place. For example, the attachment portion 12 may be attachably and detachably attached to the operation panel 114.

Incidentally, as shown in FIG. 1, the probe holder 40 may be disposed on both the left and right sides of the ultrasound diagnostic apparatus 110. In this example, the probe cable hook 10 is line-symmetric with respect to a center line in the width direction as a symmetry axis, and is line-symmetric with a center line in the thickness direction as a symmetry axis. In other words, the probe cable hook 10 of this example does not have a distinction between the front and back. With such a configuration, the probe cable hook 10 can be attached to any of the right and left probe holders 40. As a result, it is possible to further improve the general-purpose properties of the probe cable hook 10.

Figure 9A:
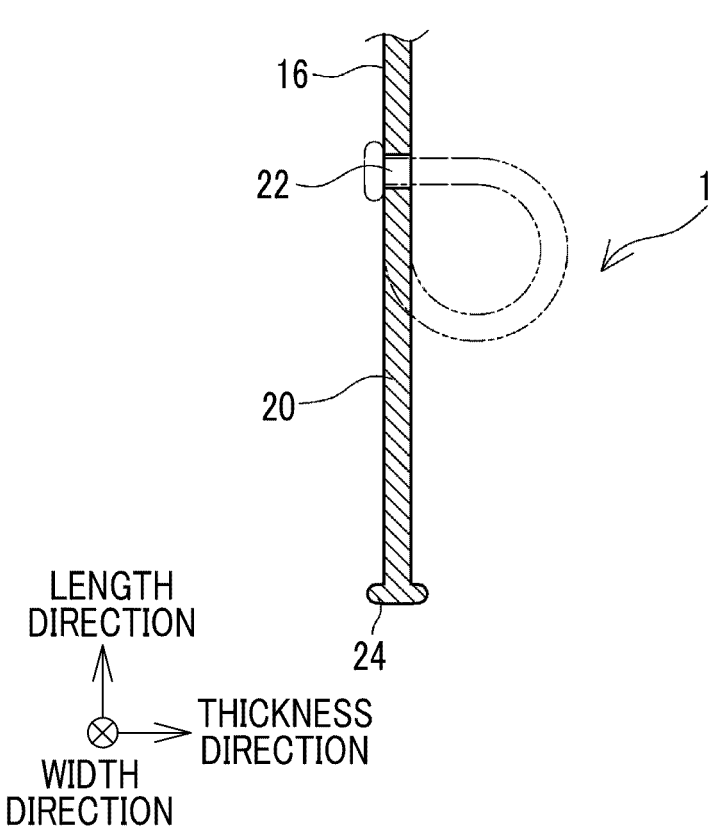
FIG. 9A is a diagram showing another example of a head portion.
Figure 9B:
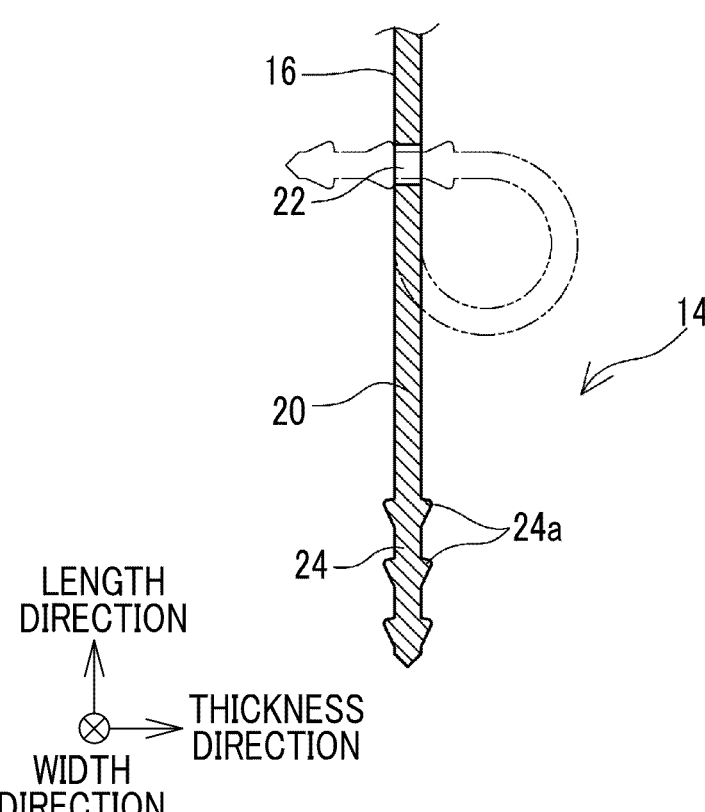
FIG. 9B is a diagram showing another example of the head portion.

In addition, the configurations of the probe cable hook 10 described so far are all examples. The probe cable hook 10 may be appropriately changed as long as it has the configuration according to claim 1. For example, the attachment portion 12, the connecting portion 16, and the hook portion 14 constituting the probe cable hook 10 does not have to be integrally formed. For example, the attachment portion 12 may be formed of another material such as metal. Further, the shape and size of each portion of the probe cable hook 10 may also be changed as appropriate. For example, the shape of the head portion 24 and the engagement hole 22 may be changed. For example, as shown in FIG. 9A, the head portion 24 may have a shape that is swollen in the thickness direction compared to the wrapping portion 20. In this case, the length direction dimension L4 of the engagement hole 22 need only be smaller than the thickness direction dimension of the head portion 24. As another aspect, as shown in FIG. 9B, a plurality of engagement protrusions 24a may be formed in the head portion 24 at intervals. Each engagement protrusion 24a has a substantially sawtooth shape that protrudes in the thickness direction. By providing a plurality of such engagement protrusions 24a, the engagement position with the engagement hole 22 can be freely changed according to the diameter of the probe cable 102.

What is claimed is:

1. A probe cable hook comprising:

an attachment portion that is attachably and detachably mounted on a part of an ultrasound diagnostic apparatus;

a hook portion consisting of a flexible material; and a connecting portion being a strap-shaped portion that extends downward from a bottom surface of the attachment portion and connects the attachment portion and the hook portion, wherein the hook portion has a wrapping portion capable of forming a loop for holding a probe cable of an ultrasound probe, the wrapping portion being formed with an engagement hole, and a head portion that is provided on an opposite side of the connecting portion with respect to the wrapping portion and is engageable with the engagement hole, and the loop is maintained by the head portion being engaged with the engagement hole, and the head portion is detached from the engagement hole by the wrapping portion receiving an outward force in a radial direction of the loop, wherein the attachment portion, the hook portion, and the connecting portion are integrally formed by the flexible material.

2. The probe cable hook according to claim 1, wherein the head portion is wider than the wrapping portion, a constricted portion having a smaller width than the wrapping portion is formed at a boundary between the head portion and the wrapping portion, and a width of the constricted portion is the same as or smaller than a width of the engagement hole.

3. The probe cable hook according to claim 1, wherein the head portion has a substantially columnar shape having an axis extending in a width direction of the probe cable hook, and a diameter of the head portion decreases toward a width direction end part.

4. The probe cable hook according to claim 1, wherein the engagement hole has a long hole shape in which a length direction dimension is larger than a width direction dimension, and a side portion, which is a portion between a width direction end part of the hook portion and a width direction end part of the engagement hole, has a length direction dimension larger than a width direction dimension.

5. The probe cable hook according to claim 1, wherein the connecting portion is narrower than the hook portion.

6. The probe cable hook according to claim 1, wherein the probe cable hook has a shape that is line-symmetric with respect to a center in a width direction of the probe cable hook as a symmetry axis and is line-symmetric with respect to a center in a thickness direction as a symmetry axis.

7. The probe cable hook according to claim 1, wherein the attachment portion is engageable with a bottom surface of a probe holder that holds the ultrasound probe, and the probe cable hook is held by being suspended from the probe holder.

8. A cable holding structure comprising:

a probe cable hook; and the probe holder that holds the ultrasound probe in a standing posture such that a cable draw-out portion of the ultrasound probe faces downward, wherein the probe cable hook comprises:

an attachment portion that is attachably and detachably mounted on a part of an ultrasound diagnostic apparatus;

a hook portion consisting of a flexible material; and a connecting portion being a strap-shaped portion that extends downward from a bottom surface of the attachment portion and connects the attachment portion and the hook portion, wherein the hook portion has a wrapping portion capable of forming a loop for holding a probe cable of an ultrasound probe, the wrapping portion being formed with an engagement hole, and a head portion that is provided on an opposite side of the connecting portion with respect to the wrapping portion and is engageable with the engagement hole, and the loop is maintained by the head portion being engaged with the engagement hole, and the head portion is detached from the engagement hole by the wrapping portion receiving an outward force in a radial direction of the loop, wherein the attachment portion is engageable with a bottom surface of a probe holder that holds the ultrasound probe, and the probe cable hook is held by being suspended from the probe holder, wherein the attachment portion has a larger size than the connecting portion in at least one of a width direction dimension or a thickness direction dimension, the probe holder has an outer cup and an inner cup that is disposed inside the outer cup, and a cable hole allowing passage of the probe cable, an accommodation recessed portion that accommodates the attachment portion, and a connection notch that extends over the cable hole and a bottom surface of the accommodation recessed portion and allows passage of the connecting portion are formed on a bottom surface of the outer cup.

* * * * *